US00PP10025P

United States Patent [19]

Mosier

[11] Patent Number: Plant 10,025

[45] Date of Patent: Sep. 9, 1997

[54] VARIETY OF GERANIUM PLANT NAMED 'BELLE'

[75] Inventor: Jennifer Mosier, Connellsville, Pa.

[73] Assignee: Oglevee, Ltd., Connellsville, Pa.

[21] Appl. No.: 579,776

[22] Filed: Dec. 28, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,360 10/1990 Guillou et al. ..... Plt./87.12

*Primary Examiner*—Howard J. Locker

*Attorney, Agent, or Firm*—Webb Ziesenheim Bruening Logsdon Orkin & Hanson, P.C.

[57] ABSTRACT

A new and distinct variety of Ivy Geranium having a better, more intense red color than Nanette. The new variety flowers earlier and its florets have more petals than either Nanette or Nicole. The new variety has more florets per umbel than either Nanette or Nicole. The new variety is more rounded and controlled than either Nanette or Nicole.

1 Drawing Sheet

BACKGROUND OF THE NEW PLANT

The present invention comprises a new and distinct cultivar of *Pelargonium×peltatum* known by the varietal name "Belle". The new variety was discovered in a selective breeding program by Jennifer Mosier. The new variety is a selection from a seedling cross from Nicole, the seed parent, ×Nanette, the pollen parent, (U.S. Plant Pat. Nos. 7,358 and 7,360, respectively).

The new cultivar was discovered in 1988 at 152 Oglevee Lane, Connellsville, Pa., and was first asexually reproduced by cuttings in January, 1989 at Connellsville, Pa. It has been found to retain its distinct characteristics through successive propagations.

The new cultivar has leaves similar to Nanette and a compactness and ability to produce more flowers similar to Nicole. The new cultivar has a more intense red than Nanette with the early flowering. The new cultivar also has more florets per umbel and the plant is more rounded and controlled than either parent.

The new cultivar, when grown in a glass greenhouse in Connellsville, Pa., using full light until May 10th at which time shade was applied to give a maximum light at 4500 F.C., 60° F. night temperature, 68° F. day temperature, 70° F. vent temperature, and grown in a peat media with constant fertilizer of 200 parts per million nitrogen and potassium, has a response time from a rooted cutting to a flowering plant in 10 cm. pot of seven weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the new cultivar. The data which define these characteristics were collected from asexual reproductions carried out by Oglevee Ltd. in Connellsville, Pa. The plants were started as rooted cuttings which were potted and then flowered seven weeks later. The plant histories were taken of plants blossomed under full light in a greenhouse and color readings were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium×peltatum.*

*Commercial.*—Ivy Geranium named "Belle".

Form: Uniform mound, free basal branching, compact.

Height: 16 to 17 cm. from pot.

Growth: Self-branching mound-like habit with some cascading.

Strength: If grown in 10 cm. pots on benches will not tangle like most ivy geraniums. Good in baskets.

Foliage: More rounded, less ivy-like leaf. Zone at base.

Leaves:

*Size.*—7 to 10 cm.

*Shape.*—Reniform, cordate base.

*Margin.*—Pedately lobed.

*Texture.*—Smooth, shiny.

*Color.*—Top: Green Group 137A; Bottom: Green Group 137D; Zone: Red Purple Group 59B.

*Ribs and veins.*—Venation: Palmate venation. Color: Green Group 138B.

Petioles:

*Length.*—5 to 7 cm.

*Color.*—Green Group 138B.

Stem:

*Color.*—Green Group 138B.

*Internodes.*—2.5 to 4 cm. in length.

THE BUD

Shape: Upright round cluster.

Size: 1 to 2.5 cm.

INFLORESCENCE

Blooming habit: Continuous, upright above foliage.

Borne: Florets on pedicel, forming an umbel on a peduncle 3 to 7 cm. above foliage.

Number of florets per umbel: 11–17.

Closed florets: Bud size: 1.25 to 1.6 cm. in length.

Size: Fully open bloom: 4 to 5 cm.

Open florets:

*Form.*—Cupped, semi-double.

*Color.*—Top: Red Group 44A; Bottom: Red Group 44D in the center, shading to Red Group 44C at the petal margin; Eye: Typically two petals, have two purple streaks, Red Purple Group 61B with eye light Purple Group 61D.

Petals: 15 to 17 in number; obovate, margin entire, separate.

Size: 1 to 1.5 cm. across; 2.5 to 3 cm. in length.

Texture and appearance: Smooth, reflective, fire engine red in color.

Petaloids:

*Quantity.*—None.

Pedicel:

*Length.*—1.75–2.25 cm.

*Color.*—Green Group 138B.

Peduncle:

*Length.*—10 to 14 cm., always from node.

*Color.*—Green Group 138B.

Persistence: Non-shattering.

Disease resistance: No known disease resistance.

Lasting quality: 10–14 days.

REPRODUCTIVE ORGANS

Stamens:

*Anthers.*—3 mm. in length, purple in color.

*Filaments.*—9 mm. in length, white to light pink in color.

*Pollen.*—Brown.

Pistils:

*Number.*—1.

*Length.*—6 mm.

*Stigma.*—Purple in color.

*Style.*—3 mm. in length.

*Ovaries.*—Color: Light green. Length: 2 mm.

Fruit: None observed.

GENERAL CHARACTERISTICS

A new geranium that improves Nanette in color by providing a cleaner, brighter, crisper and more red like tone and an improved bloom size and shape. Nicole was used as a parent because it is arguably the best ivy geranium on the market. Belle gets its flower shape, earliness and good blooming from this parent.

I claim:

1. A new and distinct variety of Ivy Geranium plant as described and shown herein and characterized by a better, more intense red color than Nanette, early flowering, has more petals on its florets, has more florets per umbel and is more rounded and controlled than either Nanette or Nicole.

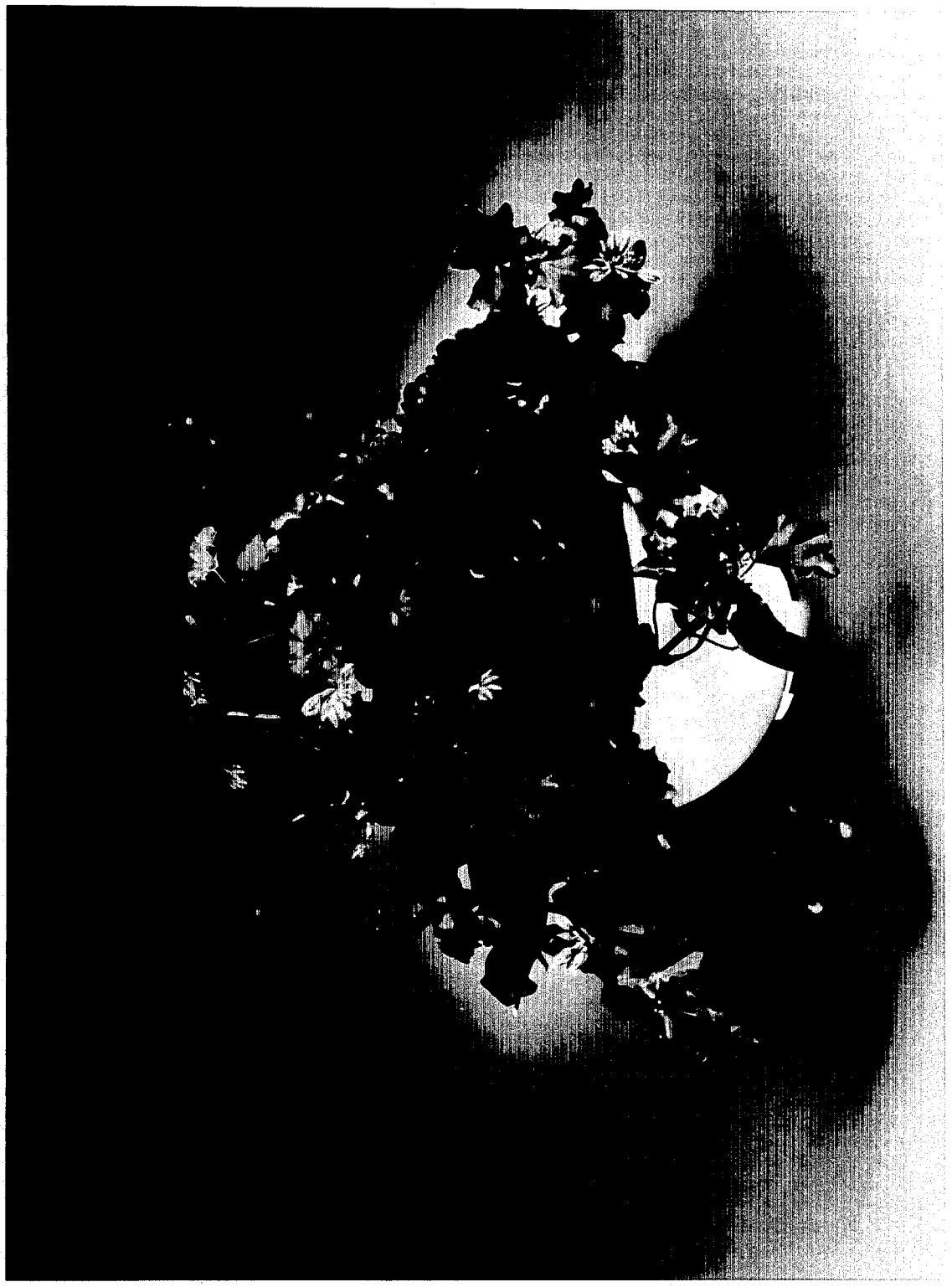

* * * * *